US009121776B2

(12) United States Patent
Chantry et al.

(10) Patent No.: US 9,121,776 B2
(45) Date of Patent: Sep. 1, 2015

(54) WELDING ARC APPAREL WITH UV OR THERMOCHROMIC ACTIVATED IMAGES

(71) Applicant: Lincoln Global, Inc., City of Industry, CA (US)

(72) Inventors: Bruce John Chantry, Solon, OH (US); Mark David McDowell, El Dorado Hills, CA (US)

(73) Assignee: Lincoln Global, Inc., City of Industry, CA (US)

( * ) Notice: Subject to any disclaimer, the term of this patent is extended or adjusted under 35 U.S.C. 154(b) by 533 days.

(21) Appl. No.: 13/645,662

(22) Filed: Oct. 5, 2012

(65) Prior Publication Data

US 2013/0026150 A1    Jan. 31, 2013

Related U.S. Application Data

(63) Continuation-in-part of application No. 12/618,231, filed on Nov. 13, 2009, now Pat. No. 8,284,385.

(51) Int. Cl.
*G01K 11/00*    (2006.01)
*G01K 11/12*    (2006.01)
(Continued)

(52) U.S. Cl.
CPC ............... *G01K 11/12* (2013.01); *A61F 9/067* (2013.01); *B23K 9/322* (2013.01); *C09D 11/50* (2013.01); *F16P 1/06* (2013.01); *G01J 1/429* (2013.01); *G01J 1/58* (2013.01)

(58) Field of Classification Search
CPC ......... G01K 13/08; G01K 13/02; G01K 1/14; G01K 1/022; G01K 1/24; G01K 7/42; G01K 7/01; G01K 11/13; G01K 11/32; G01K 11/165; G01K 11/12

USPC ......... 374/120, 121, 141, 160, 161, 162, 186; 116/216
See application file for complete search history.

(56) References Cited

U.S. PATENT DOCUMENTS 3,597,054 A    8/1971  Winter
4,066,567 A *  1/1978  Labes ........................... 374/102
(Continued)

FOREIGN PATENT DOCUMENTS

CA    2637105 A1    3/2009
CN    201323898 Y    10/2009
(Continued)

OTHER PUBLICATIONS

International Search Report for application PCT/IB2010/02908, dated Apr. 15, 2011.
(Continued)

*Primary Examiner* — Lisa Caputo
*Assistant Examiner* — Nathaniel T Woodward
(74) *Attorney, Agent, or Firm* — Hahn, Loeser & Parks, LLP

(57) ABSTRACT

A welding accessory and a system for detecting thermal and/or UV radiation exposure during welding operations are disclosed. The welding accessory may have a surface exposed to thermal and/or UV radiation generated by electric arc welding, a first image visible without exposure to the thermal and/or UV radiation, and a second image formed from either a UV activated dye that is visible only after exposure to UV radiation generated by the electric welding arc or a thermochromic dye that is visible only after exposure to a predetermined level of thermal radiation generated by the welding arc. A system may include either a thermal or UV exposure indicator with a first state and at least a second state, and include either a thermochromic or UV activated dye adapted to provide a reversible or persistent visual indication upon exposure to radiation. The visual indication may include any combination of symbols, logos, images, text, or other decorative or informational designs as desired.

17 Claims, 7 Drawing Sheets

(51) Int. Cl.

| | |
|---|---|
| A61F 9/06 | (2006.01) |
| F16P 1/06 | (2006.01) |
| G01J 1/58 | (2006.01) |
| G01J 1/42 | (2006.01) |
| C09D 11/50 | (2014.01) |
| B23K 9/32 | (2006.01) |

(56) References Cited

U.S. PATENT DOCUMENTS

| | | | |
|---|---|---|---|
| 4,255,665 | A | 3/1981 | Shriner |
| 4,788,433 | A | 11/1988 | Wright |
| 4,882,598 | A | 11/1989 | Wulf |
| 5,499,597 | A * | 3/1996 | Kronberg .................. 116/216 |
| 5,500,532 | A | 3/1996 | Kozicki |
| 5,612,541 | A | 3/1997 | Hoffmann et al. |
| 5,731,589 | A | 3/1998 | Sief et al. |
| 5,986,273 | A | 11/1999 | Tripp et al. |
| 6,017,661 | A | 1/2000 | Lindsay et al. |
| 6,054,256 | A | 4/2000 | Nohr et al. |
| 6,060,223 | A | 5/2000 | Nohr et al. |
| 6,132,681 | A | 10/2000 | Faran et al. |
| 6,437,346 | B1 | 8/2002 | Goudjil |
| 6,818,904 | B1 | 11/2004 | Ferren et al. |
| 7,462,443 | B2 | 12/2008 | Willard et al. |
| 7,589,331 | B2 | 9/2009 | Havens et al. |
| 7,658,722 | B2 | 2/2010 | Cude |
| 7,709,812 | B2 | 5/2010 | Simon et al. |
| 2004/0182284 | A1 | 9/2004 | Belykh et al. |
| 2008/0185534 | A1 | 8/2008 | Simon et al. |
| 2008/0296513 | A1 | 12/2008 | Ribi et al. |
| 2009/0194708 | A1 | 8/2009 | Studer et al. |
| 2009/0224168 | A1 | 9/2009 | Santibanez-Viani et al. |
| 2010/0012017 | A1 * | 1/2010 | Miller ........................ 116/201 |
| 2011/0116076 | A1 | 5/2011 | Chantry et al. |

FOREIGN PATENT DOCUMENTS

| | | |
|---|---|---|
| DE | 29715067 U1 * | 12/1997 |
| DE | 10112122 C1 | 10/2002 |
| EP | 1123814 A2 | 8/2001 |
| EP | 1637046 A2 | 3/2006 |
| WO | 96/39302 | 12/1996 |
| WO | 2008037076 A1 | 4/2008 |
| WO | 2011058431 A2 | 5/2011 |
| WO | 2012058470 A1 | 5/2012 |

OTHER PUBLICATIONS

Written Opinion for application PCT/IB2010/02908, dated Apr. 15, 2011.

Kober, Paul A., The Use of Dyes as Temperature Indicators', Industrial and Engineering Chemistry, pp. 837 & 838, vol. 15, No. 8, dated Aug. 1923.

Dennis, John H., et al, The Effects of Welding Parameters on Ultraviolet Light Emissions, Ozone and CRVI Formation in MIG Welding, Department of Environmental Science, University of Bradford, Bradford BD7 1DP, U.K., Ann. occup. Hyg., vol. 41, No. 1, pp. 95-104, copyright 1997.

Lyon, Terry L., Knowing the Dangers of Actinic Ultraviolet Emissions, The Welding Journal, Dec. 28, 2002.

Sliney, D.H., Transparent Welding Curtains, The Welding Journal, May 18, 1982.

Hallcrest Handbook of Thermochromic Liquid Crystal Technology, dated 1991.

International Preliminary Report on Patentability for PCT/IB2013/002206 dated Apr. 16, 2015.

International Search Report and Written Opinion for PCT/IB2013/002206 dated Apr. 17, 2014.

* cited by examiner

WELDING ARC APPAREL WITH UV OR THERMOCHROMIC ACTIVATED IMAGES

CROSS-REFERENCE TO RELATED APPLICATIONS

This application claims priority from U.S. patent application Ser. No. 12/618,231 filed on 13 Nov. 2009, the application being hereinby fully incorporated by reference.

TECHNICAL FIELD OF THE INVENTION

The present disclosure relates to welding accessories, and more specifically, to welding apparel with images activated by UV radiation from an electric welding arc or with images activated at various welding exposure temperatures.

BACKGROUND OF THE INVENTION

Welding is an important process in the manufacture and construction of various products and structures. Applications for welding are widespread and used throughout the world including, for example, the construction and repair of ships, buildings, bridges, vehicles, and pipe lines, to name a few. Welding is performed in a variety of locations, such as in a factory with a fixed welding operation or on site with a portable welder.

In manual or semi-automated welding a user/operator (i.e. welder) directs welding equipment to make a weld. For example, in electric arc welding the welder may manually position a welding rod or welding wire and produce a heat generating arc at a weld location. In this type of welding, the spacing of the electrode from the weld location is related to the arc produced and to the achievement of optimum melting/fusing of the base and welding rod or wire metals. The quality of such a weld is often directly dependent upon the skill of the welder.

The electric welding arc is known to produce ultraviolet (UV) radiation as well as thermal (heat) radiation. The UV radiation produced by the electric welding arc is capable of causing injury comparable to a sun burn. The UV radiation has also been known to cause eye irritation, a condition commonly referred to as "welder's flash" or "arc eye." The intensity of the UV radiation produced during electric arc welding depends upon many factors such as the process type, welding parameters, electrode and base metal composition, fluxes, and any coating or plating on the base metal. Additionally, tip size, shielding gas, and filler metal composition are among other variables that affect the amount of UV radiation generated. In addition to direct exposure to UV radiation, UV radiation can reflect from surfaces common in a welding environment, such as unpainted metals and concrete floors, resulting in indirect exposure. Further, the effects of UV radiation exposure are cumulative and repeated exposure can result in retinal injury and other health hazards.

The produced thermal (heat) radiation may equally be detrimental to the welder, and excess amounts can be reflective of improper setup of the welding operation, or improper welding technique or a myriad of other technical and/or user-related issues. Therefore, detecting heat exposure, particularly threshold temperatures, is also important in that it may be reflective of the need for a welder to take a break.

UV radiation is commonly divided into three bands, UV-A, UV-B, and UV-C, in order of decreasing wavelength. Natural sunlight is the most prevalent source of UV radiation in all three bands, however UV-C is substantially absorbed by the ozone layer. Generally UV-A has a wavelength from 320 to 380 nanometers; UV-B has a wavelength from 290 to 320 nanometers; and UV-C has a wavelength from 200 to 290 nanometers. The shorter the wavelength the greater the biological effects of the UV radiation. Electric arc welding produces UV radiation in all three bands, but has substantial emissions in the upper end of the UV-C band.

In the past, various methods and devices have been used to shield welders from the UV radiation and/or heat produced by electric arcs. For example, welding helmets, jackets, and gloves are customarily worn that substantially shield the welder from heat or block UV radiation from reaching the welder's eyes and body. In the welding environment, other personnel also commonly wear personal protective equipment such as safety glasses that limit exposure to UV radiation and/or generated heat.

The extent of UV exposure for personnel working around welding arcs varies greatly and is often not precisely known. To limit unintended exposure to nearby persons, curtains and shields of various types have been constructed to isolate the welding operation. The reflection of UV radiation from unpainted metal, concrete, and other surfaces however limits the effectiveness of shielding the welding operation. Welding operations have also been located away from walkways, aisles, and other areas where other personnel are working to reduce exposure to the other personnel, however, this is often impractical when welding operations are conducted in confined areas. Other techniques for avoiding UV exposure have also been employed including placing warning signs around the welding environment highlighting the potential for UV exposure.

SUMMARY OF THE INVENTION

This present disclosure relates to welding accessories that are capable of providing a visual indication of the presence of UV radiation and/or thermal (heat) radiation energy generated by an electric welding arc during a welding operation. The welding accessories may, for example, include welding helmets, welding jackets, welding shirts, hard hats, cloth skull caps, ball cap style hats, safety glasses, gloves, badges, work boots, belts, and jewelry, in addition to other accessories used in a welding environment. The visual indication may be a transition between a first image and a second image, and the transition may be permanent or reversible. The welding accessory may be a welding helmet, welding jacket, gloves, safety glasses, indicator badge, or other welding accessory. One or more UV activated dyes, pigments or inks are employed to provide the indication in the presence of UV radiation from the electric welding arc. Additionally, one or more thermochromic dyes, pigments, paints or inks are employed to provide the indication of a certain temperature exposure by the welder to the welding operation. It must be understood, as used in this application the term "UV activated dye" is to include UV activated dyes, pigments, inks and any other similar substance. A UV exposure indicator may also have a first state and at least a second state, where the visual indication is a transition between the first state and at least the second state. Various symbols, logos, text, images, or other decorative or informational designs may be employed to indicate the presence or absence of UV radiation. Similarly, a "thermochromic" reaction includes a reversible or irreversible color change upon either accumulated exposure to heat energy or to meeting a threshold value for a specified temperature.

Also disclosed is a system for detecting cumulative UV radiation exposure or cumulative heat exposure during welding operations having a UV exposure indicator or thermochromic exposure indicator with graduated states.

Various aspects of the present disclosure will become apparent to those skilled in the art from the following detailed description and the accompanying drawings.

DETAILED DESCRIPTION OF THE INVENTION

Figure 1:
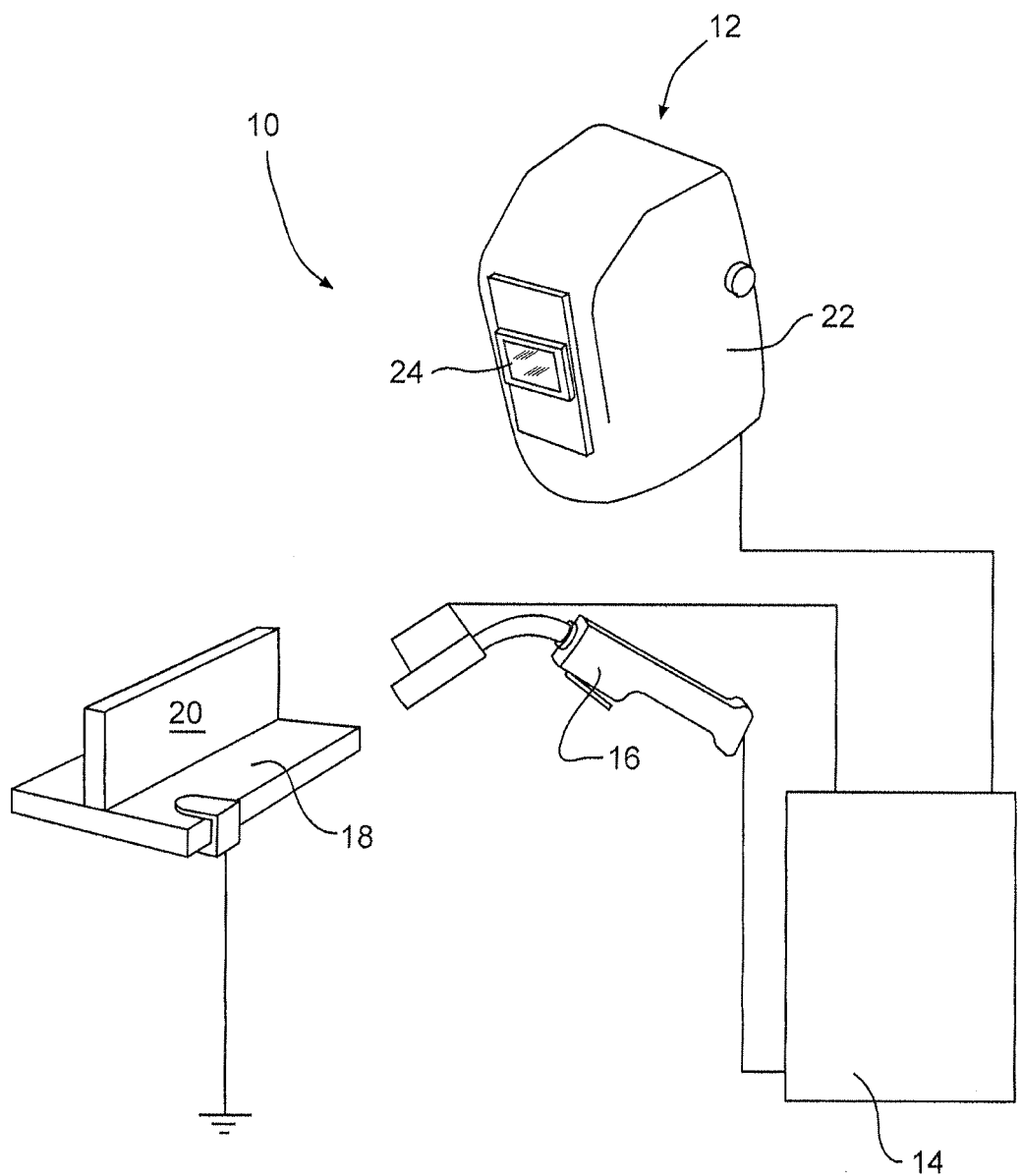
FIG. 1 is a schematic view of a welding environment.

Referring now to the drawings, FIG. 1 illustrates a welding environment 10. The welding environment 10 includes welding helmet 12, welding system 14, welding gun 16, and workpiece 18. The welding environment may also, for example, include a stick electrode holder, TIG torch or other apparatus for use with electric arc welding. Workpiece 18 generally defines a welding work area 20 where the welding gun may be used to form a weld. Various non-limiting types of exemplary welding, including Shielded Metal Arc Welding (SMAW), Gas Metal Arc Welding (GMAW) e.g. MIG melding, and Gas Tungsten Arc Welding (GTAW) e.g. TIG welding, may be conducted in the welding environment.

Welding system 14 includes welding equipment for generating a welding current and voltage, a welding control system for controlling the welding current and voltage, and a monitoring system for monitoring the welding current and voltage. The monitoring system may also monitor a variety of other operating parameters, such as but not limited to, welding wire feed speed, amount of welding wire remaining, any type of welding feedback desired by the operator, and any other desired operating parameters.

The discussion pertinent to FIGS. 1-7 pertains to UV activated materials as well as to heat activated materials, e.g., thermochromic materials. Presently disclosed is a welding accessory comprising a surface exposed to an electric welding arc during a welding operation, the surface having a first image and a second image, the first image being visible on the surface of the welding accessory without exposure to the electric welding arc, and the second image formed from UV activated dye on the surface and visible only after exposure to UV radiation generated by the electric welding arc during the welding operation. The welding accessory may be welding helmets, welding jackets, welding shirts, safety glasses, gloves, badges, work boots, belts, or jewelry, or any other suitable accessories used or worn in a welding environment that may have a surface exposed to UV radiation. When pertinent to heat, it should be recognized that heat flows spontaneously from systems of higher temperature to systems of lower temperature. When two systems come into thermal contact, they exchange energy through the microscopic interactions of their particles. When the systems are at different temperatures, this entails spontaneous net flow of energy from the hotter to the cooler, so that the hotter decreases in temperature and the cooler increases in temperature. This will continue until their temperatures are equal. Then the net flow of energy has settled to zero, and the systems are said to be in a relation of thermal equilibrium. Spontaneous heat transfer is an irreversible process.

During operation, welding system 14 operates to generate an electric welding arc between welding gun 16 and workpiece 18. In other examples, welding system 14 may generate an electric welding arc between a stick electrode holder, a GTAW or TIG torch or another welding apparatus and the workpiece 18. In each example, the electric welding arc generates electromagnetic radiation including emissions in the UV, visible light, and infrared spectra as well as heat energy. The UV radiation generated by the electric welding arc may include radiation in the UV-A, UV-B, and UV-C bands. Frequently, the UV radiation produced by electric welding arcs may be concentrated in the UV-C band between approximately 200 and 290 nanometers in wavelength. The UV radiation may be further concentrated between approximately 260 and 280 nanometers in wavelength.

A welding accessory may have a first image visible on the surface of the welding accessory without exposure to the electric welding arc. For example, the first image may be a logo, symbol, text, or other decorative or informational design. Alternatively, the first image may be the undecorated surface of the welding accessory. For example, the outer surface 22 of the welding helmet 12 may have a first image such as a company logo.

A welding accessory may also have a second image formed from UV activated dye or pigment on the surface of the welding accessory, where the second image is visible only after exposure to UV radiation generated by the electric welding arc during the welding operation. Similar considerations are applicable to temperature-sensitive paints, dyes and/or pigments. The second image may also be a logo, symbol, text, or other decorative or informational design as desired. For example, the second image may be a warning symbol indicating the presence of UV radiation or may be a warning indicative of exposure to at least a predetermined amount of UV radiation. Similarly, the second image may be formed upon exposure to a temperature which is considered as too high for a proper welding environment. In another example, the second image may be a decorative design identifying the provider of the welding accessory.

Figure 2:
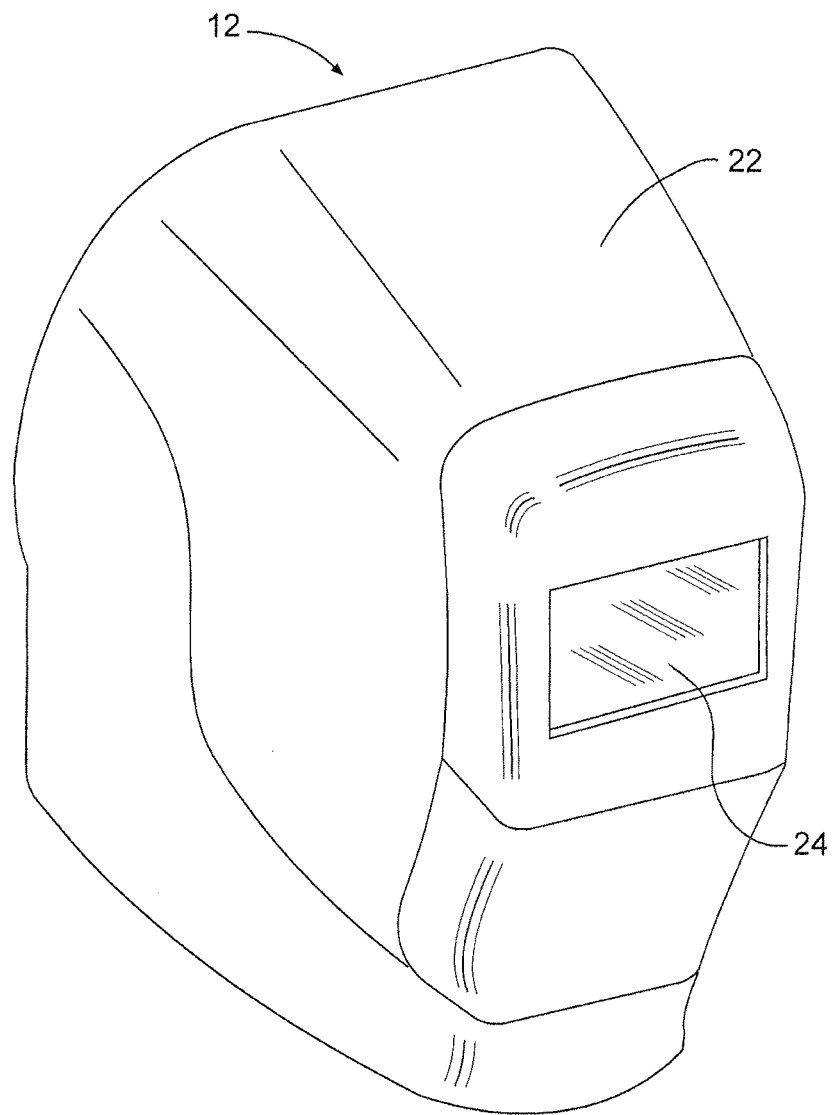
FIG. 2 is a perspective view of a welding helmet.
Figure 3:
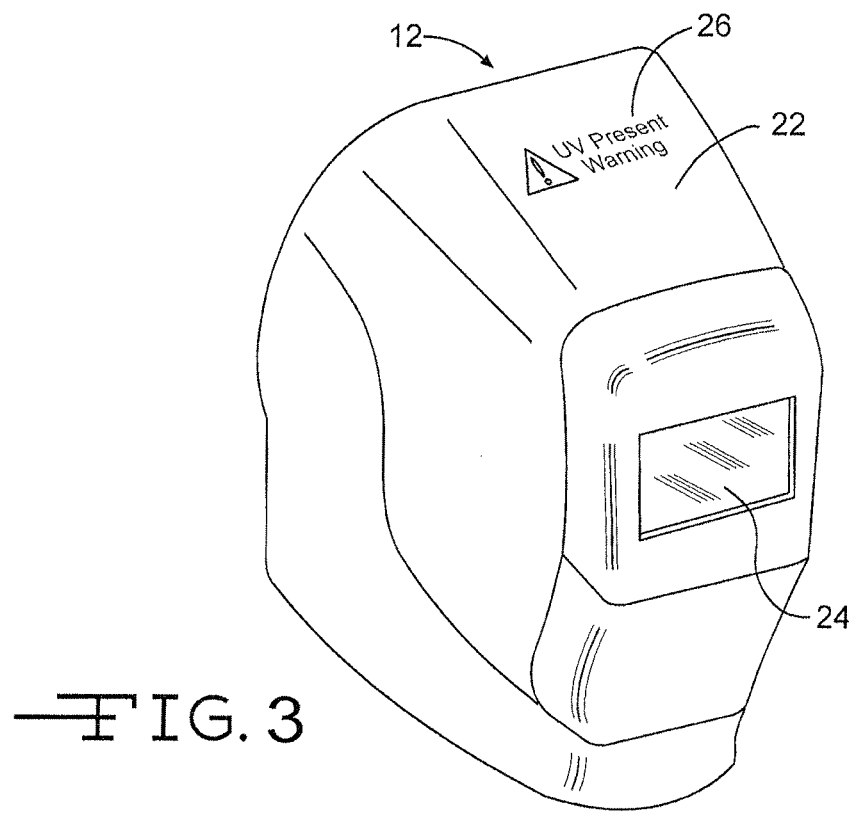
FIG. 3 is a perspective view of a welding helmet after exposure to UV radiation.
Figure 4:
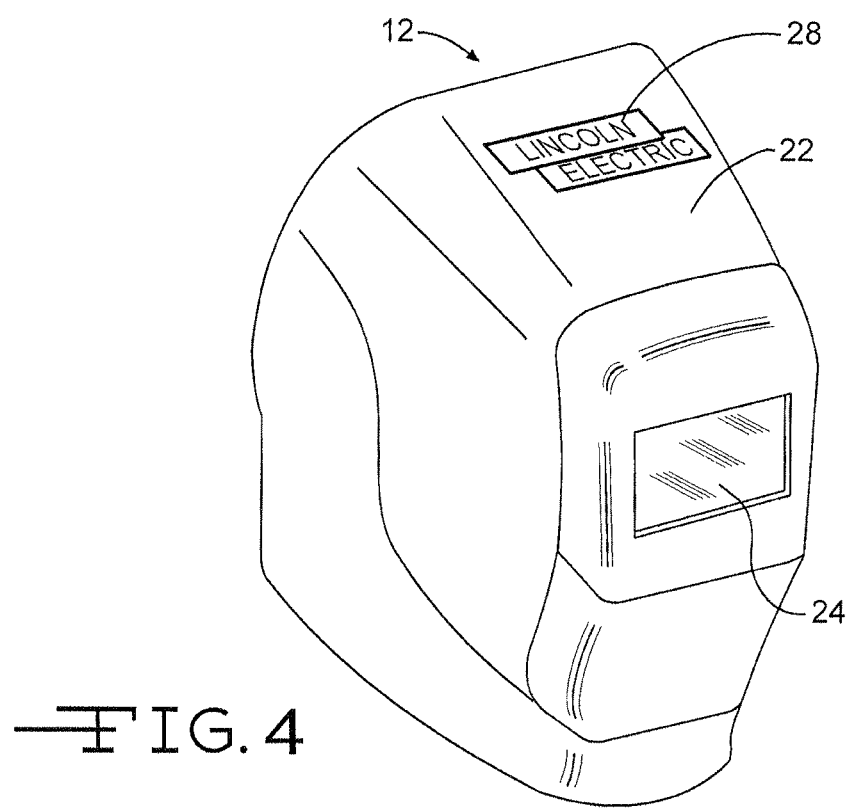
FIG. 4 is a perspective view of another welding helmet after exposure to UV radiation.

Referring to FIGS. 2-4, welding helmet 12 is illustrated having outer surface 22 and view port 24. Welding helmet 12 shields the welder's head and eyes from the electric welding arc, the UV radiation, and heat generated by the electric welding arc. Welding helmet 12 may also protect the welder from sparks and other hazards commonly encountered in a welding environment. Outer surface 22 of welding helmet 12 is exposed to the electric welding arc during the welding operation.

As shown in FIG. 2, outer surface 22 has a first image which in one aspect of the invention, is the undecorated surface of the welding helmet. Outer surface 22 also has a second image formed from either a UV activated material or a thermochromic material. The second image may be a warning symbol 26 such as that illustrated in FIG. 3. The second image may be a company logo 28 such as that illustrated in FIG. 4. As will be apparent, the second image may be selected from numerous designs as desired.

The second image is formed from either a UV activated material or a thermochromic material which is affixed on the surface of the welding accessory. In one aspect, the second image is integrated into the material forming the surface of the welding accessory. Alternatively, the second image is applied to the surface of the welding accessory. In yet another alternative, the UV activated material or thermochromic material is incorporated into a UV exposure indicator or a temperature indicator, and attached to the surface of the welding accessory in the form of a badge, sticker, or other comparable device.

A UV activated dye or pigment may generally be described as a substance that undergoes a change of color or state upon exposure to UV radiation. UV activated dyes have also been referred to as photochromatic, photochangeable, and photoreactive dyes. As used herein, the term UV activated dye is intended to represent substances that undergo a change of color or state upon exposure to UV radiation. Various UV activated dyes are known and commercially available, and are contemplated for use with the present disclosure. UV activated dyes that respond to UV radiation but are stable in the presence of natural sunlight or artificial lights are known. The UV activated dyes may be selected to respond to specific wavelengths of UV radiation. For example, a UV activated dye may be selected to respond to wavelengths between 200 and 290 nanometers. In another example, a UV activated dye may be selected to respond to wavelengths between 260 and 280 nanometers. A combination of UV activated dyes and non-activated materials may be utilized to provide the desired characteristics. These and other known UV activated dyes may be employed with the present disclosure.

As known in the art, one UV activated dye, an irreversible ultraviolet radiation transorber that is erasable/mutable, is exemplified by an ultraviolet radiation transorber/mutable colorant/molecular includant complex where the mutable colorant is malachite green or Victoria Pure Blue BO (Basic Blue 7) and, the ultraviolet radiation transorber is IRGACURE 184 (1-hydroxycyclohexyl phenyl ketone), and the molecular includant is β-cyclodextrin.

In further examples, an exemplary and non-limiting list of mutable colorants includes triarylmethyl dyes, such as Malachite Green Carbinol base {4-(dimethylamino)-α-[4-(dimethylamino)phenyl]-α-phenylbenzene-methanol}, Malachite Green Carbinol hydrochloride {N-4-[[4-(dimethylamino)phenyl]phenylmethylene]-2,5-cyclohexyldien-1-ylidene]-N-methyl-methanaminium chloride or bis[p-(dimethylamino)phenyl]phenylmethylium chloride}, and Malachite Green oxalate {N-4-[[4-(dimethylamino)phenyl]phenylmethylene]-2,5-cyclohexyldien-1-ylidene]-N-methylmethanaminium chloride or bis[p-(dimethylamino)phenyl]phenylmethylium oxalate}; monoazo dyes, such as Cyanine Black, Chrysoidine [Basic Orange 2; 4-(phenylazo)-1,3-benzenediamine monohydrochloride], Victoria Pure Blue BO, Victoria Pure Blue B, basic fuschin and β-Naphthol Orange; thiazine dyes, such as Methylene Green, zinc chloride double salt [3,7-bis(dimethylamino)-6-nitrophenothiazin-5-ium chloride, zinc chloride double salt]; oxazine dyes, such as Lumichrome (7,8-dimethylalloxazine); naphthalimide dyes, such as Lucifer Yellow CH {6-amino-2-[(hydrazinocarbonyl)amino]-2,3-dihydro-1,3-dioxo-1H-benz[de]isoquinoline-5,8-disulfonic acid dilithium salt}; azine dyes, such as Janus Green B {3-(diethylamino)-7-[[4-(dimethylamino)phenyl]azo]-5-phenylphenazinium chloride}; cyanine dyes, such as Indocyanine Green {Cardio-Green or Fox Green; 2-[7-[1,3-dihydro-1,1-dimethyl-3-(4-sulfobutyl)-2H-benz[e]indol-2-ylidene]-1,3,5-heptatrienyl]-1,1-dimethyl-3-(4-sulfobutyl)-1H-benz[e]indolium hydroxide inner salt sodium salt}; indigo dyes, such as Indigo {Indigo Blue or Vat Blue 1; 2-(1,3-dihydro-3-oxo-2H-indol-2-ylidene)-1,2-dihydro-3H-indol-3-one}; coumarin dyes, such as 7-hydroxy-4-methylcoumarin (4-methylumbelliferone); benzimidazole dyes, such as Hoechst 33258 [bisbenzimide or 2-(4-hydroxyphenyl)-5-(4-methyl-1-piperazinyl)-2,5-bi-1H-benzimidazole trihydrochloride pentahydrate]; paraquinoidal dyes, such as Hematoxylin {Natural Black 1; 7,11b-dihydrobenz[b]indeno[1,2-d]pyran-3,4,6a,9,10(6H)-pentol}; fluorescein dyes, such as Fluoresceinamine (5-aminofluorescein); diazonium salt dyes, such as Diazo Red RC (Azoic Diazo No. 10 or Fast Red RC salt; 2-methoxy-5-chlorobenzenediazonium chloride, zinc chloride double salt); azoic diazo dyes, such as Fast Blue BB salt (Azoic Diazo No. 20; 4-benzoylamino-2,5-diethoxybenzene diazonium chloride, zinc chloride double salt); phenylenediamine dyes, such as Disperse Yellow 9 [N-(2,4-dinitrophenyl)-1,4-phenylenediamine or Solvent Orange 53]; diazo dyes, such as Disperse Orange 13 [Solvent Orange 52; 1-phenylazo-4-(4-hydroxyphenylazo)naphthalene]; anthraquinone dyes, such as Disperse Blue 3 [Celliton Fast Blue FFR; 1-methylamino-4-(2-hydroxyethylamino)-9,10-anthraquinone], Disperse Blue 14 [Celliton Fast Blue B; 1,4-bis(methylamino)-9,10-anthraquinone], and Alizarin Blue Black B (Mordant Black 13); trisazo dyes, such as Direct Blue 71 {Benzo Light Blue FFL or Sirius Light Blue BRR; 3-[(4-[(4-[(6-amino-1-hydroxy-3-sulfo-2-naphthalenyl)azo]-6-sulfo-1-naphthalenyl)azo]-1-naphthalenyl)azo]-1,5-naphthalenedisulfonic acid tetrasodium xanthene dyes, such as 2,7-dichlorofluorescein; proflavine dyes, such as 3,6-diaminoacridine hemisulfate (Proflavine); sulfonaphthalein dyes, such as Cresol Red (o-cresolsulfonaphthalein); phthalocyanine dyes, such as Copper Phthalocyanine {Pigment Blue 15; (SP-4-1)-[29H,31H-phthalocyanato(2-)-$N^{29},N^{30},N^{31},N^{32}$]copper}; carotenoid dyes, such as trans-.beta.-carotene (Food Orange 5); carminic acid dyes, such as Carmine, the aluminum or calcium-aluminum lake of carminic acid (7-a-D-glucopyranosyl-9,10-dihydro-3,5,6,8-tetrahydroxy-1-methyl-9,10-dioxo-2-anthracenecarbonylic acid); azure dyes, such as Azure A [3-amino-7-(dimethylamino)phenothiazin-5-ium chloride or 7-(dimethylamino)-3-imino-3H-phenothiazine hydrochloride]; and acridine dyes, such as Acridine Orange [Basic Orange 14; 3,8-bis(dimethylamino)acridine hydrochloride, zinc chloride double salt] and Acriflavine (Acriflavine neutral; 3,6-diamino-10-methylacridinium chloride mixture with 3,6-acridinediamine).

As known in the art, a non-limiting and exemplary list of the irreversible ultraviolet radiation transorber may include a stabilizing compound, such as, phthaloylglycine-2959, DARCUR 2959, and other photoreactors such as 1-hydroxy-cyclohexyl-phenyl ketone ("HCPK") (IRGACURE 184, Ciba-Geigy); α,α-dimethoxy-α-hydroxy acetophenone (DAROCUR 1173, Merck); 1-(4-isopropylphenyl)-2-hydroxy-2-methyl-propan-1-one (DAROCUR 1116, Merck); 1-[4-(2-hydroxyethoxy)phenyl]-2-hydroxy-2-methyl-propan-1-one (DAROCUR 2959, Merck); poly[2-hydroxy-2-methyl-1-[4-(1-methylvinyl)phenyl]propan-1-one] (ESACURE KIP, Fratelli Lamberti); benzoin (2-hydroxy-1,2-diphenylethanone) (ESACURE BO, Fratelli Lamberti); benzoin ethyl ether (2-ethoxy-1,2-diphenylethanone) (DAITOCURE EE, Siber Hegner); benzoin isopropyl ether (2-isopropoxy-1,2-diphenylethanone) (VICURE 30, Stauffer); benzoin n-butyl ether (2-butoxy-1,2-diphenylethanone) (ESACURE EB1, Fratelli Lamberti); mixture of benzoin butyl ethers (TRIGONAL 14, Akzo); benzoin iso-butyl ether (2-isobutoxy-1,2-diphenylethanone) (VICURE 10, Stauffer); blend of benzoin n-butyl ether and benzoin isobutyl ether (ESACURE EB3, ESACURE EB4, Fratelli Lamberti); benzildimethyl ketal (2,2-dimethoxy-1,2-diphenylethanone) ("BDK") (IRGACURE 651, Ciba-Geigy); 2,2-diethoxy-1,2-diphenylethanone (UVATONE 8302, Upjohn); α,α-diethoxyacetophenone (2,2-Diethoxy-1-phenyl-ethanone)

("DEAF", Upjohn), (DEAF, Rahn); and α,α-di-(n-butoxy)-acetophenone (2,2-dibutoxyl-1-phenylethanone) (UVA-TONE 8301, Upjohn)

Several examples of photochromic agents include diynes (conjugated diacetylenes), and in particular acid, ester, urethane, amide, nitrile, or alcohol monomers of at least about 8 carbon atoms, and not more than about 36 carbon atoms, more usually from about 12 to 30 carbon atoms. These acetylenic groups may generally be displaced from the terminal carbon atoms by at least 1 carbon atom. Various derivatives of the functional groups of the diynes can serve to modify the properties of the diynes for use in a particular formulation. A transparent UV activated paint/polish may be made by adding the monomer 10,12-pentacosadiyneoic, acid (PDA) to a clear commercially available nail polish finish (such as Orly Snap, Orly International, Inc., made with ethyl acetate, butyl acetate, isopropyl alcohol, nitrocellulose, dibutylphthalate, polyvinyl butyral, etocrylene, D&C red #6 barium lake, D&C violet #2) or to a commercially available clear coat paint to a final concentration of 100 PDA/ml polish/paint finish. The PDA monomer was mixed to clarity. Thin films may then be applied to surfaces to be exposed to UV radiation. Also, stick-on sensor tabs may include transparent tape stickers (e.g. ¼ inch in diameter circles made with acrylic based adhesive label dye cut and placed on a convenient removal strip) coated with a solution of 100 mg PDA/ml chloroform with a coating thickness of about 200 microns.

For example, one non-limiting example of a suitable photochrome for UV dye is a spirooxazine. The spiro form of an oxazine is a colorless leuco dye; the conjugated system of the oxazine and another aromatic part of the molecule is separated by a $sp^3$-hybridized "spiro" carbon. After irradiation with UV light, the bond between the spiro-carbon and the oxazine breaks, the ring opens, the spiro carbon achieves $sp^2$ hybridization and becomes planar, the aromatic group rotates, aligns its π-orbitals with the rest of the molecule, and a conjugated system forms with ability to absorb photons of visible light, and therefore appear colorful. When the UV source is removed, the molecules gradually relax to their ground state, the carbon-oxygen bond reforms, the spiro-carbon becomes $sp^3$ hybridized again, and the molecule returns to its colorless state. This example illustrates a reversible color-change.

In another non-limiting example, a suitable UV is a UV sensitive composition that undergoes a color change upon exposure to a predetermined dosage of UV-C radiation. The UV-C sensitive composition includes a halogenated polymer, such as polyvinylidene chloride, that produces an acid upon exposure to UV radiation, and a pH sensitive dye. Upon exposure to UV-C radiation, the halogenated polymer undergoes degradation and produces HCl. The pH sensitive dye changes color as a result in an increase in HCl in the system. This composition may also include an acid scavenging composition and/or a diluent to control the amount of HCl produced in the system. The amount of HCl liberated from UV-C exposure may be selectively controlled so that a color change may be produced at a desired UV-C dosage. This example illustrates a unidirectional color change.

A halogenated polymer may be used, such as polyvinyl chloride (PVC), polyvinylidene chloride (PVDC), ethylene-chlorotrifluoroethylene copolymer, chlorinated rubber, and copolymers thereof and in some cases the halogenated copolymers may also be combined with one or more monomers that have little or no halogen content. The pH sensitive dye may be bromophenol blue, phenol red, thymol blue, ethyl orange, m-Cresol purple, New Fuchsin, p-methyl red, lissamine green, aniline blue, methyl violet, crystal violet, ethyl violet, brilliant green, oralochite green oxalate, methyl green, cresol red, quinaldine red, para methyl red, bromothymol blue, metanil yellow, orange IV, phenylazoaniline, erythrosin B, benzopurpurin 4B, congo red, methyl orange, resazurin, methyl red, alizarin red, bromocresol purple, chlorophenol red, or combinations of dyes for multiple color changes.

In a further non-limiting example, the UV dye may be a "diarylethen." Diarylethens generally have a high thermodynamic stability. Diarylethens operate by means of a 6-π electrocyclic reaction, the thermal analog of which is impossible due to steric hindrance. Some other photochromic dyes have the appearance of a crystalline powder, and in order to achieve the color change, they may have to be dissolved in a solvent or dispersed in a suitable matrix. However, some diarylethenes require so little shape change upon isomerization that they have the advantage that they may be converted between states while remaining in crystalline form.

Additionally, the UV dye may be Spectrachrome® crystals, U.S. trademark Reg. No. 2,531,301 registered to Del Sol, L.C. In this example, among others, the dye may be employed into thread to be embroidered on to an article.

As used in the application, a "thermochromic material" or "thermochromic composition" is a composition which changes color with temperature. There are generally two types of thermochromic systems: those based on liquid crystals and those which rely on molecular rearrangement. In either case, at a given temperature, a change in the structure of the material occurs giving rise to an apparent change in color. The change is preferably reversible so as the material cools down, it changes color back to its original state. In liquid crystals, the change from colored to transparent state occurs over a small temperature range, typically less than about 5° C., more preferably less than about 3° C., and even more preferably less than about 1° C. The change arises as the crystals in the material change their orientation. With molecular rearrangement, typically leucodyes are employed and the active temperature range of the dye is controlled by changing the chemical groups on the corners and central site of the molecule. Leucodyes have a broader temperature change range than liquid crystals.

In both cases, the thermochromic material is typically (but not required to be) encapsulated inside microscopic spherical particles to protect it. These encapsulating molecules must themselves be transparent and able to withstand the thermal cycling which the thermochromic material will experience.

In practice, the thermochromic material does not generally produce two or more colors itself. The encapsulated particles of the material are printed onto or mixed into another material in the second color. At room temperature, the sample is the color of the thermochromic dye, but when it is heated above its transition temperature, the thermochromic material becomes transparent, thus showing the bae color underneath. For example, if a layer of red thermochromic pigment is applied to a blue substrate at room temperature, it will appear red, but as it warms up, it becomes blue. As the temperature decreases again, the red color will reappear.

As used herein, one non-limiting and exemplary illustration of one aspect of the invention involves a "leuco dye" which often refers to a dye which, prior to development, is referred to as the leuco form which is substantially colorless or white, and which reacts with another substance upon exposure to heat to form a colored dye. The color-altering phenomenon is typically due to a chemical change, such as through oxidation, resulting from heat exposure.

The term "activator" refers to a composition that is interactive or reactive with leuco dyes upon introduction of heat.

The term "acid-generating source" includes compositions that react under the influence of either heat or IR radiation to provide either acids or radicals which form acids.

As used herein, "developing" or "development" refers to the interaction or reaction of a leuco dye with another agent, such as an activator, to produce a visible composition having a desired color.

As used herein, "absorber" refers generally to an electromagnetic radiation sensitive agent that can generate heat upon exposure to a predetermined frequency of electromagnetic radiation. The predetermined frequency can be different from one absorber composition to the next. When admixed with or in thermal contact with a leuco dye and/or activator, an absorber can be present in sufficient quantity so as to produce heat sufficient to at least partially develop the leuco dye in accordance with embodiments of the present invention.

The term "thermal contact" refers to the spatial relationship between an absorber and a color forming composition. For example, when an absorber is heated by interaction with electromagnetic radiation, the heat generated by the absorber should be sufficient to cause the leuco dye of the color forming composition to darken through reaction with the activator. Thermal contact can include close proximity between an absorber and a leuco dye, which allows for heat transfer from the absorber toward the leuco dye and/or activator. Thermal contact can also include actual contact between an absorber and a leuco dye, such as in immediately adjacent layers, or in an admixture including both constituents.

"Stabilizing agent" refers to compositions that can be used to reduce undesired development of leuco dyes upon exposure to ambient or other light sources.

"Carrier" or "liquid carrier" is defined to include liquid compositions that can be used to carry leuco dyes, activators, stabilizing agents, and/or absorbers to a substrate. Water, surfactants, solvents, cosolvents, and the like can be used in various combinations as the liquid carrier. A combination of leuco dye, activators, acid-generating source, absorber, and stabilizing agent can be within a common liquid carrier, or can be in multiple separate carriers to be applied to a substrate sequentially. The liquid carrier can also carry other additives such as polymers, UV curable materials, and/or colorant in some embodiments.

The term "spin-coatable composition" includes a liquid carrier having various components dissolved or dispersed therein. In some embodiments, the spin-coatable composition can comprise a color forming composition, an absorber, and a stabilizing agent in a common liquid carrier. In other embodiments, fewer components can be present in a liquid carrier forming the spin-coatable composition. Alternatively, multiple liquid carriers can be used to carry the color forming composition, the absorber, and the stabilizing agent in any combination, wherein at least one of the color forming composition, the absorber, and the stabilizing agent is spin-coatable. It is important to note that a spin-coatable composition that lists various components does not require that all components of the composition be independently spin-coatable. In other words, if at least one component of a spin-coatable composition having multiple components is described as spin-coatable, the entire composition is defined as spin-coatable for purposes of the present disclosure. Thus, for example, the color forming composition can be spin-coatable and applied to a substrate and then a stabilizing agent can be formed in a separate layer which can be applied by spraying, screen-printing, or other methods which do not require spin-coatability. When referring to spin-coatable compositions herein, it is to be understood that this designation is provided for exemplary purposes only. Coating compositions can be spin-coatable in one embodiment, or can be configured for other application methods as well.

It is noted that, with respect to leuco dyes, activators, acid-generating sources, absorbers, stabilizing agents, and other non-liquid carrier components, the weight percent values are measured relative to a dry basis, thus excluding the liquid carrier. In other words, unless otherwise specified, values of "% by weight" or "weight percent" refer to the compositions that will be present in the color forming composition, excluding the carrier (typically MEK and/or an alcohol). Thus, such values are measured based on the dry weight percent of the coating composition, prior to adding to admixture with the liquid carrier to form a spin-coatable composition. The total dry coating weight can include leuco dye, activator, acid-generating source, absorber, stabilizing agent, binder, plasticizer, and other optional additives. It should be noted that some of the listed components can be undissolved solids, and some components can dissolve, e.g., stabilizing agents, etc., when mixed with typical solvent carriers.

One exception to the above description of weight percent occurs when referring to "solids." The term "solids" refers to the components of a composition that are not dissolved in the liquid carrier. Typically, leuco dyes, activators, acid-generating sources, stabilizing agents, and/or absorbers will remain on a substrate after drying of the liquid carrier, but as these components are typically solubilized in the liquid carrier, they are not included as solids. Additives such as pigments, polymers, plasticizers, and the like can be dispersed in the liquid carrier, rather than dissolved, and make up the solids content. This distinction is useful to understand, as the total amount of solids by weight in the color forming composition (which includes the carrier) has an upper limit in order for the composition to be spin-coatable. In one embodiment, the total percentage of solids in the color forming composition can be less than 10% by weight.

Concentrations, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 μm to about 200 μm should be interpreted to include not only the explicitly recited concentration limits of 1 μm to about 200 μm, but also to include individual concentrations such as 2 μm, 3 μm, 4 μm, and sub-ranges such as 10 μm to 50 μm, 20 μm to 100 μm, etc.

The thermochromic aspect of the invention relates generally to labeling a welding component as used by a welder using specific coating compositions which can optionally be spin-coatable. The coating compositions of the present invention, which can optionally be spin-coatable, can be prepared and applied in a variety of ways to a variety of substrates. For example, a spin-coatable composition can be prepared that includes a liquid carrier (which will be substantially removed upon drying) that contains, without limitation, a leuco dye, a hexaarylbiimidazole activator, an acid-generating source, an electromagnetic radiation absorber, and a stabilizing agent. The spin-coatable composition includes the liquid carrier, which can act to improve coating performance, but which can be removed upon coating through known liquid removal processes. Typically, at least a portion of the liquid carrier can be driven off or allowed to evaporate after the coating process is complete. The liquid carrier can include, but is not limited to, solvents such as methylethyl ketone, isopropyl alcohol or other alcohols, water, surfactants, and mixtures thereof.

In an alternative embodiment, the electromagnetic radiation absorber can be applied in a separate layer with respect to a color forming layer, e.g., leuco dye, activator, acid-generating composition, wherein the separate layer is placed on the substrate either before or after the color forming composition.

In one aspect of the invention, a color forming composition can be applied as its own layer, or can be applied with an absorber and/or stabilizer. The color forming composition can include a leuco dye, an activator, and an acid-generating source. In one aspect of the invention, non-limiting and exemplary leuco dyes suitable for use in the present invention are members selected from the group consisting of amino-triarylmethanes, aminoxanthenes, aminothioxanthenes, amino-9,10-dihydro-acridines, aminophenoxazines, aminophenothiazines, aminodihydro-phenazines, aminohydrocinnamic acids and corresponding esters, 2(p-hydroxyphenyl)-4,5-diphenylimidazoles, indanones, and mixtures thereof. In one aspect of the present invention, the leuco dye is an aminotriarylmethane such as Leuco Crystal Violet having the structure:

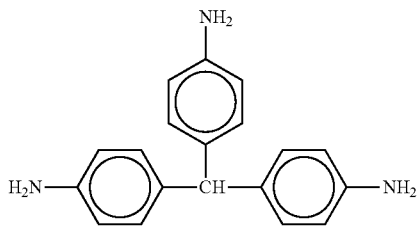

Generally, leuco dyes are substantially colorless, and upon removal of one or two hydrogen atoms, convert to a colored dye. A wide variety of specific leuco dyes within the above mentioned categories may be suitable for use in the present invention and are known to those skilled in the art.

Upon heat-induced oxidation, protonation, ring-opening, or the like, in the presence of an activator, the above-recited leuco dyes can form dyes having a variety of optical characteristics. Although a wide range of compositions are suitable for use in the present invention, the coating composition can contain at least about 3% by weight of leuco dye, and in more detail, can be present at from about 4% and about 20% by weight. This weight ratio range assumes that the color forming composition (which includes the leuco dye), absorber, and stabilizing agent are in a common coating layer, which can be optionally spin-coatable. However, one skilled in the art would recognize that this ratio can be altered if the color forming composition is applied as a separate layer with respect to the absorber and/or the stabilizer. These ranges are only exemplary and other weight ranges can be used depending on the desired image characteristics and other considerations.

As stated, interaction between a leuco dye and an activator causes a chemical change in the leuco dye, thereby altering the color of the leuco dye from substantially white or colorless to substantially colored in appearance. The colored appearance can be generally a dark color such as black or deep colors having a high optical density. Generally, the chemical change in the leuco dye occurs upon application of a predetermined amount of heat. Activators suitable for use in the present invention are generally known as hexaarylbiimidazoles (HABIs) and can be chosen by those skilled in the art. Several non-limiting examples of suitable HABI activators include 2,2'-bis(2-ethoxyphenyl)-4,4',5,5'-tetraphenyl-2',1,1'-bi-1H-imidazole (o-EtO-HABI); 2-(o-chlorophenyl)-4,5-bis(m-methoxyphenyl)imidazole dimer (CMD-HABI); 2,2'-bis(2-chlorophenyl)-4,4',5,5'-tetraphenyl-1,1'-bi-1H-imidazole (o-CI-HABI); 2-(2-methylphenyl)-2'-[2-(2-methylphenyl)-4,5-diphenyl-2H-imidazol-2-yl]-4,5-diphenyl-1H-imidazole (o-Me-HABI); 2,2',5-tris(2-chlorophenyl)-4-(3,4-dimethoxyphenyl)-4',5'-diphenylbiimidazole (TCDM-HABI); 2,2',4,4'-tetra(2-chlorophenyl)-5,5'-bis(3,4-dimethoxyphenyl)-2',1'-bi-1'-1H-imidazole (TCTM-HABI); 2,2'-di(2'-naphthalenyl)-4,4',5,5'-tetraphenyl-1,1'-bi-1H-imidazole (N-HABI); 2,2'-bis(1-naphthalenyl)-4,4'-bis(2-chlorophenyl-5,5'-bis(3-methoxyphenyl)-2',1'-bi-1H-imidazole (MCN-HABI); and 2,2'-bis(1-naphthalenyl)-4,4',5,5'-tetrakis(3-methoxyphenyl)-2,1'-bi-1H-imidazole (MN-HABI), and combinations thereof. In one aspect of the present invention, the HABI activator is o-EtO-HABI. Other HABI activators can be used in the present invention and are known to those skilled in the art. The coating compositions of the present invention can contain from about 6% to about 45% by weight of HABI activator in one embodiment. In another embodiment, the HABI activator can be present from about 20% and about 40% by weight. In a further detailed aspect, the HABI activator can be present at from about 25% to about 38% by weight. However, if the coating composition is applied in layers, which layers can be individually spin-coatable, including a layer wherein the color forming composition is not applied in a common liquid carrier as the absorber and/or the stabilizing agent, these range values can be altered as would be apparent to one skilled in the art.

In another aspect of the present invention, the color forming composition can also include an acid-generating compound. The acid-generating compound can be configured to react under the influence of either heat or IR radiation to provide either acids or radicals which form acids. The acid-generating compounds suitable for use in the present invention include halogen sources such as, but not limited to, tribromomethylphenyl sulfone, 1,2-dibromotetrachloroethane, tristrichloromethyltriazine, dibromobenzylidene acetophenone, and mixtures thereof. In one aspect of the present invention, the halogen source can be tribromomethylphenyl sulfone.

An electromagnetic radiation absorber can be part of the coating composition, and can be applied as a separate layer which can be optionally spin-coatable, or can be applied in a common liquid carrier with the color forming composition and/or the stabilizing agent. The absorber can act as an energy antenna, providing heat to surrounding areas upon interaction with an energy source. As a predetermined amount of heat is provided by the electromagnetic radiation absorber, matching of the electromagnetic radiation frequency and intensity to the absorber used can be carried out to optimize the system. The absorber can be present in the spin-coatable composition in an amount of between about 0.001% and about 10% by weight, and typically, between about 1% and about 5% by weight, although other weight ranges may be desirable depending on the activity of the particular absorber. As stated previously, these weight percentages represent an amount of absorber that can be present in a single layer spin-coatable composition. These weight percentages can be altered in other embodiments, such as when the absorber is applied separately with respect to one or more other layers.

Various absorbers will act as an antenna to absorb electromagnetic radiation of specific frequencies and ranges. The absorber can be configured to be in a heat-conductive relationship with the leuco dyes of the present invention. For example, the absorber can be placed in the same layer as the leuco dye as part of an admixture, or can be in a separate layer. Thus, the absorber can be admixed with or in thermal contact with the color forming composition. In one aspect of the present invention, the absorber can be applied to the substrate in a separate adjacent layer prior to or after applying the color forming composition as a layer. In one embodiment, consideration can also be given to choosing the absorber such that any light absorbed in the visible range does not adversely affect the graphic display or appearance of undeveloped leuco dye.

Although an inorganic compound can be used, the absorber typically can be an organic compound, such as, but is not limited to polymethyl indoliums, metal complex IR dyes, indocyanine green, heterocyclic compounds and combinations thereof. Suitable polymethyl indolium compounds include 2-[2-[2-chloro-3-[2-(1,3-dihydro-1,3,3-trimethyl-2H-indol-2-ylidene)-ethylidene]-1-cyclopenten-1-yl-ethenyl]-1,3,3-trimethyl-3H-indolium perchlorate; 2-[2-[2-chloro-3-[2-(1,3-dihydro-1,3,3-trimethyl-2H-indol-2-ylidene)-ethylidene]-1-cyclopenten-1-yl-ethenyl]-1,3,3-trimethyl-3H-indolium chloride; 2-[2-[2-chloro-3-[(1,3-dihydro-3,3-dimethyl-1-propyl-2H-indol-2-ylidene)ethylidene]-1-cyclohexen-1-yl]ethenyl]-3,3-dimethyl-1-propylindolium iodide; 2-[2-[2-chloro-3-[(1,3-dihydro-1,3,3-trimethyl-2H-indol-2-ylidene)ethylidene]-1-cyclohexen-1-yl]ethenyl]-1,3,3-trimethylindolium iodide; 2-[2-[2-chloro-3-[(1,3-dihydro-1,3,3-trimethyl-2H-indol-2-ylidene)ethylidene]-1-cyclohexen-1-yl]ethenyl]-1,3,3-trimethylindolium perchlorate; 2-[2-[3-[(1,3-dihydro-3,3-dimethyl-1-propyl-2H-indol-2-ylidene)ethylidene]-2-(phenylthio)-1-cyclohexen-1-yl]ethenyl]-3,3-dimethyl-1-propylindolium perchlorate; and mixtures thereof. In one aspect of the present invention, the IR absorber is 2-[2-[2-chloro-3-[2-(1,3-dihydro-1,3,3-trimethyl-2H-indol-2-ylidene)-ethylidene]-1-cyclopenten-1-yl-ethenyl]-1,3,3-trimethyl-3H-indolium perchlorate. Other suitable absorbers can also be used in the present invention and are known to those skilled in the art. Although, the specific activators and absorbers discussed herein are separate compounds, such activity can also be provided by constituent groups of a leuco dye which incorporates the activation and/or radiation absorbing action within the leuco dye molecule.

A stabilizing agent can also be included in the coating compositions of the present invention which can be optionally spin-coatable. In accordance with one aspect of the present invention, the stabilizing agent can be included in the color forming composition. In another aspect, the stabilizing agent can be present in a separate layer, and applied to the substrate after the color forming composition. The present invention makes use of a stabilizing agent which comprises a diarylguanidine dye salt to improve ambient light stability. Suitable diarylguanidine dye salts include salts of yellow, brown, and orange dyes having acid groups and a diarylguanidine such as diphenylguanidines, di-o-tolylguanidines, dixylylguanidines, and di-o-oxylguanidines. In one embodiment, the stabilizing agent is an admixture of a salt of metanil yellow or tartrazine, and di-o-tolyl-phenyl guanidine. The structure of both compositions of the admixture are shown below.

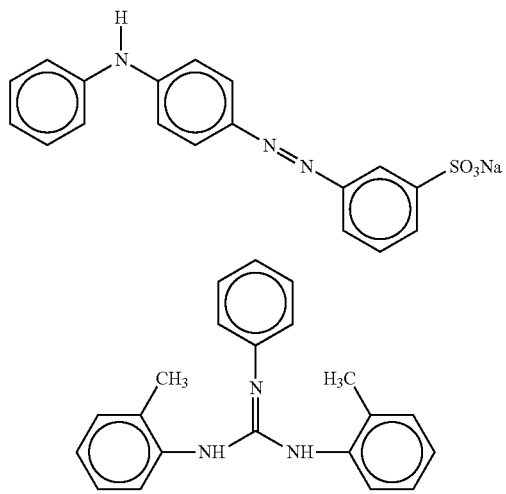

In one aspect of the invention, the di-o-tolylphenyl guanidine yellow dye not only significantly increased room light stability, but can provide a good "background" color which was not excessively dark (though the di-o-tolyl-phenyl guanidine yellow dye is not technically present as a background, as it is either admixed within the leuco dye layer, or is present as part of a layer coated atop the leuco dye layer). Other suitable diarylguanidine dye salts includes the commercially available LUXOL dyes such as LUXOL Fast Brown K/G, LUXOL FAST YELLOW T, LUXOL Fast Orange GS, other LUXOL dyes, and similar compounds. Other colored dyes such as LUXOL Fast Red, Black, Blue and the like can also be used. In one embodiment, the stabilizing agent can be mixed with a binder such as a cellulosic ester binder to form an overcoat composition. This overcoat composition can be applied to a suitable substrate subsequent to the color forming composition layer.

The stabilizing agent can be present in the spin-coatable composition at from about 5% by weight to about 20% by weight, and in one aspect from about 7% to about 15% by weight, such as about 10% by weight. Again, these weight ratios assume that the stabilizing agent is present with the color forming composition and the absorber in a common layer. One skilled in the art would recognize that, if applied as a separate layer, these ranges could be altered. For example, an overcoat layer can contain from about 10% to about 20% by weight stabilizing agent.

In a more detailed aspect of the present invention, the stabilizing agent can further include a polyhydroxybenzophenone, hydroxylamine, triarylimidazole, hydroxyphenylbenzotriazole, and mixtures thereof. In one aspect of the present invention the stabilizing agent further comprises 2,2',4,4'-tetrahydroxybenzophenone. In another aspect, the stabilizer further comprises a dibenzyl-hydroxylamine. Such additional stabilizers can be present up to about 20% by weight, independent of the above diarylguanidine dye salts. If present in a separate layer, these weight percentages can be altered.

Typically, the activator and the leuco dye are present in a common layer, and thus, concentration ratios can be considered for a desired effect. However, if the color forming composition comprises multiple layers itself, proximity can be considered.

There are many optional ingredients that can be present in the spin-coatable compositions of the present invention. For example, a binder can also be included in the compositions of the present invention, either in single layer or multiple layer embodiments. Suitable binders are known to those skilled in the art and can include, but are not limited to, polymeric materials such as polyacrylate from monomers and oligomers, polyvinyl alcohols, polyvinyl pyrrolidines, polyethylenes, polyphenols or polyphenolic esters, polyurethanes, acrylic polymers, and mixtures thereof. In order to provide desirable color forming properties, various factors such as viscosity and solids content can be considered. The spin-coatable compositions of the present invention can have less than about 10% by weight of solids, which typically provides good coating properties. For example, in one aspect, the solids content of the spin-coatable composition can be about 7% by weight.

It can be sometimes desirable to add a plasticizer to improve coating flexibility, durability, and coating performance. Plasticizers can be either solid or liquid plasticizers. Such suitable plasticizers are well known to those skilled in the art. If the leuco dye, activator, acid-generating source, absorber, and/or stabilizing agent are applied in a common liquid carrier, the plasticizer and binder can be included in the carrier as well. If the leuco dye, activator, acid-generating source, stabilizing agent, and/or absorber are applied in multiple layers, the plasticizer and binder can be included in from any one to all of individual liquid carriers.

Other variations can also be implemented, including the adding of a non-leuco colorant to impart additional desired color to the image. For example, the use of an opacifier pigment or other non-leuco colorant can be used to provide background color. The non-leuco colorants can be added to the coating composition (which can include a color forming composition layer, an activator layer, and stabilizing agent layer, or can be an admixture of the three layers in one or two layers), or the protective layer(s), as long as the development of the leuco dye is not prevented from at least some development due to the presence of the optional colorant. In another embodiment, portions of the leuco dye can then be developed producing an image with a colored background. Examples of opacifiers include calcium carbonate, titanium dioxide, and other known opacifiers. Additionally, examples of other non-leuco colorants include dyes or other pigments. In other words, if a colored background is desired that will remain independent of leuco dye development, an opacifier pigment, other pigment, and/or dye can be admixed in the carrier to impart the desired color.

In preparing the color forming composition, such the ingredients can be prepared in solution which is substantially transparent or translucent. Any suitable liquid carrier, such as an alcohol or surfactant, can be used which is compatible with a particular leuco dye (and other ingredients) chosen for use. When the color forming composition is prepared in a solution form, it may be desirable to underprint a colored coating over at least a portion of the substrate beneath the leuco dye solution. The optional colored coating produces a background color that is visible underneath the solution layer. This colored coating can contain various non-leuco colorants such as other pigments and/or dyes. Alternatively, a non-leuco colorant may be added to the data layer to produce the desired background color. The activator can be admixed within the solution or coated onto the substrate either before or after the solution is coated thereon. If a background color is preprinted, such coatings and compositions can be applied to the substrate using any of a variety of known techniques such as screen-printing, spin coating, sputtering, or spray coating. Each coating may be applied and then dried sequentially. In addition, such colored coatings may be applied over the color forming compositions of the present invention. It has been found that improved ambient light stability is achieved when a colored overcoat is applied to the color forming compositions of the present invention.

Both leuco dyes and liquid crystals are limited in their temperature sensing range. Shifting to more inorganic-based thermochromic compositions increases the upper temperature sensing limit and allow a working temperature sensing environment of at least approximately 100-500° F.

Non-limiting, exemplary examples of higher temperature thermochromic materials include: crystals of heavy metals of Groups I, II, III, IV, V, VI, VII, VIII of the Periodic Table, and as the binder—mixtures or pure components based on silicates, borates, phosphates of alkali or alkaline earth metals, the weight ratio of the thermochromic component to binder being from 2:98 to 98:2.

For intensification of the thermochromic features, thermostable, non-thermochromic or low-thermochromic components may be added.

Exemplary, non-limiting examples of the thermochromic component include: (i) compositions based on bismuth oxide compound of the general formula $(Bi_2O_3)_{1-z}(M_xO_y)_z$ wherein z ranges from 0-0.5, wherein M is selected from the group consisting of heavy, alkali, alkaline earth metals and mixtures thereof—for example, M may be selected from the following: Zr (IV), Hf(IV), Sn(II), Sn(IV), Nb(V), Ta(V), Mo(VI), W(VI), Cr(III), Cr(VI), Mn(II), Fe(III), Co(II), Ni(II), Pb(II), Ca(II), Sr(II), Ba(II), Li, Na, K, Rb, Cs; (ii) compositions based on niobates and tantalates of general formula $(M_xO_y)_m(Bi_2O_3)_nNb(Ta)_2O_5$, wherein m ranges from 0-1, n ranges from 1-2, and wherein M is selected from the group consisting of heavy, alkali, alkaline earth metals and mixtures thereof—for example, M may be selected from the following: Na, K, Rb, Cs, Mg, Ca, Sr, Ba, Pb(II), Co (II), Ni(II), Cr(III), Cu(II), Cu(I); (iii) compositions based on molybdates and tungstates of the general formula $(M_xO_y)_m(Bi_2O_3)_nMo(W)O_3$ wherein m ranges from 0-1, n ranges from 0-12, and further wherein M is selected from the group consisting of alkali, alkaline earth, heavy metals and mixtures thereof—for example, M may be selected from the following: Na, K, Rb, Cs, Mg, Ca, Sr, Ba, Sn, Ti, Zr, Pb(II), Mn(II), Mn(III), Co(II), Ni (II), Cr(III), Cu(II); (iv) compositions based on chromates, molybdates, and tungstates of general formula $(M_xO_y)_m(Me_xC_y)_nMo(W,Cr)O_3$ wherein m=ranges from 0-1, n ranges from 0-1, and further wherein M is selected from the group consisting of alkali, alkaline earth, heavy metals and mixtures thereof, Me is a heavy metal—for example, M may be selected from the following: Na, K, Pb, Cs, Mg, Ca, Sr, Ba, Sn, Ti, Zr, Pb(II), and examples of Me are Cu(II), Mn(II), Mn(III), Co(II), Ni(II), Cr(III); (v) compositions based on niobates and tantalates of general formula $(M_xO_y)_m(Me_xO_y)_nNb(Ta)_2O_5$, wherein m ranges from 0-1, n ranges from 0-1, and further wherein M is selected from the group consisting of alkali, alkaline earth, heavy metals and mixtures thereof, and Me is selected from the group consisting of Cu(II), Mn(II), Mn(III), Co(II), Ni(II), Cr(III)—for instance, M is Na, K, Rb, Cs, Mg, Ca, Sr, Ba, Sn, Ti, Zr, Pb(II).

An example of stable non-thermochromic or low thermochromic pigment is blue cobalt, $CoAl_2O_4$ or $CoWO_4$ or $Co_{1-x}Zn_xWO_4$ or $CoMoO_4$ and for the thermochromic compound $Bi_2O_3$ or the compounds are selected from (ii) and (iii). Another example is the mixture of $(Bi_2O_3)_x(CrO_3)_x$ as a thermochromic component and $Cr_2O_3$ as thermostable pigment. The ratio of the quantity of thermochromic compound to thermochromic pigment is in the range of from 50:1 to 1:30.

Without being held to any one theory or mode of operation, the phenomenon of thermochromism is connected with phase transition in solid state (polymorphic transformation). Typical representatives of solid thermochromic compounds of this type are some of iodomercurates, iodides of thallium, mercury, and silver, which have a clear and reversible color change in the point of phase transition. These compounds have high contrast of color changes with temperature, but they are stable only at low temperatures. For most thermochromic compounds, such as $Ag_2HgI_4$ have a maximum allowable temperature of 200° C.

During a welding operation, the electric welding arc generates heat and UV radiation that reaches a surface of the welding accessory. The thermochromic or UV activated material forming the second image on the surface of the welding accessory responds to the heat or UV radiation causing the second image to appear indicating the presence of heat or UV radiation. The first image and second image may be selected to highlight the presence of heat or UV radiation or may be selected for other reasons.

Figure 5A:
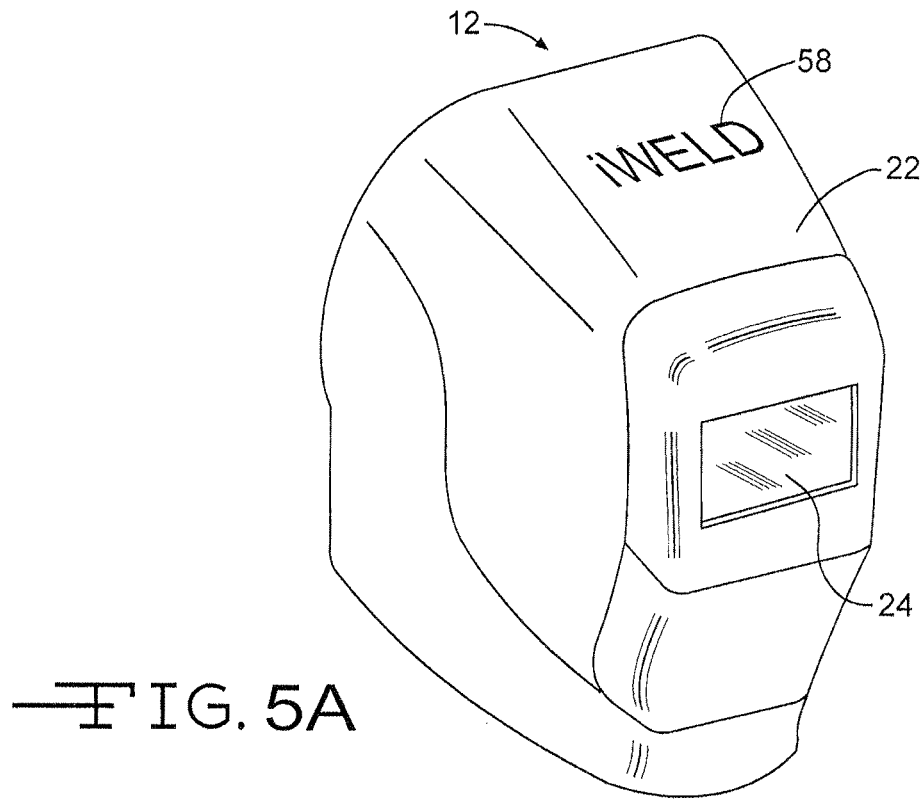
FIGS. 5A-B are perspective views of yet another welding helmet.
Figure 5B:
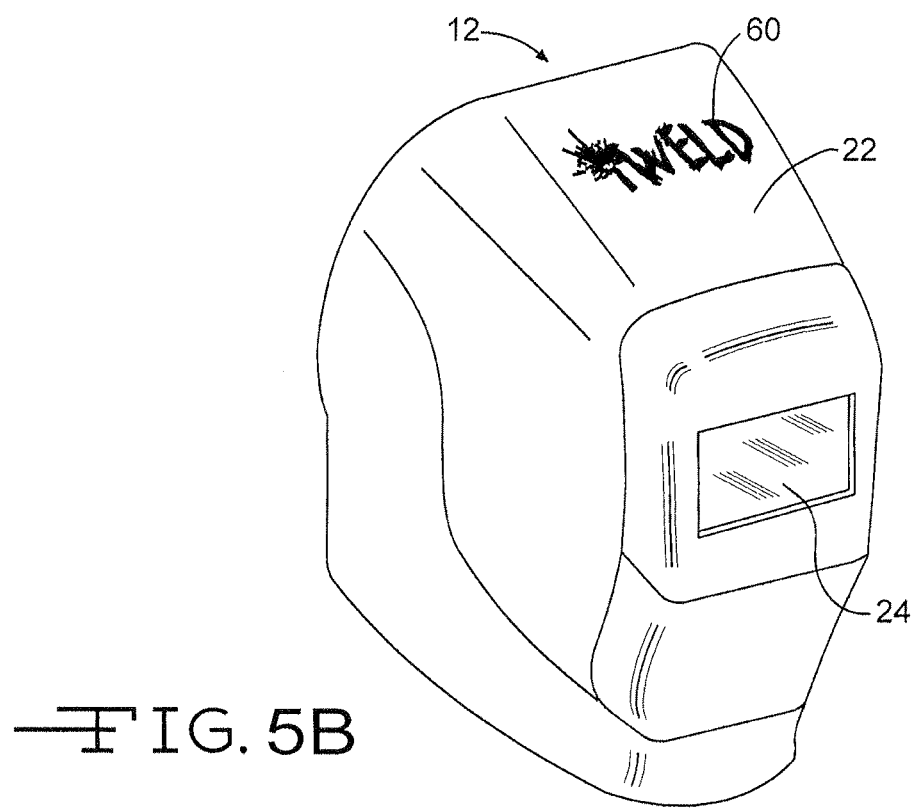

Other embodiments include a variety of other welding accessories. For example, referring generally to FIGS. 5A and 5B, another welding helmet 12 is illustrated. Welding helmet 12 has a primary image 58 visible without exposure to the electric welding arc as shown in FIG. 5A. Welding helmet 12 also has secondary image 60 formed from a thermochromic or UV activated dye as shown in FIG. 5B. As the figures illustrate, the first image and the second image may overlap. Also, the first image and the second image may combine to form a composite image on the surface of the welding accessory. This combination of the first image and the second image permits integration of various logos, symbols, text, and other decorative or informational designs when applied to the welding accessories.

Figure 6A:
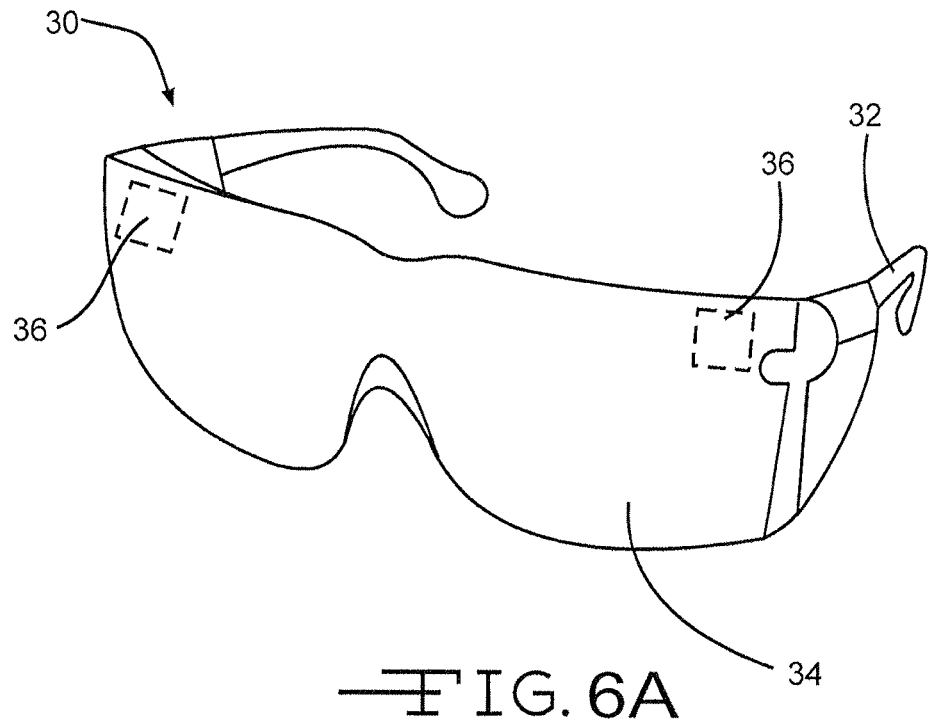
FIGS. 6A-B are perspective views of safety glasses.
Figure 6B:
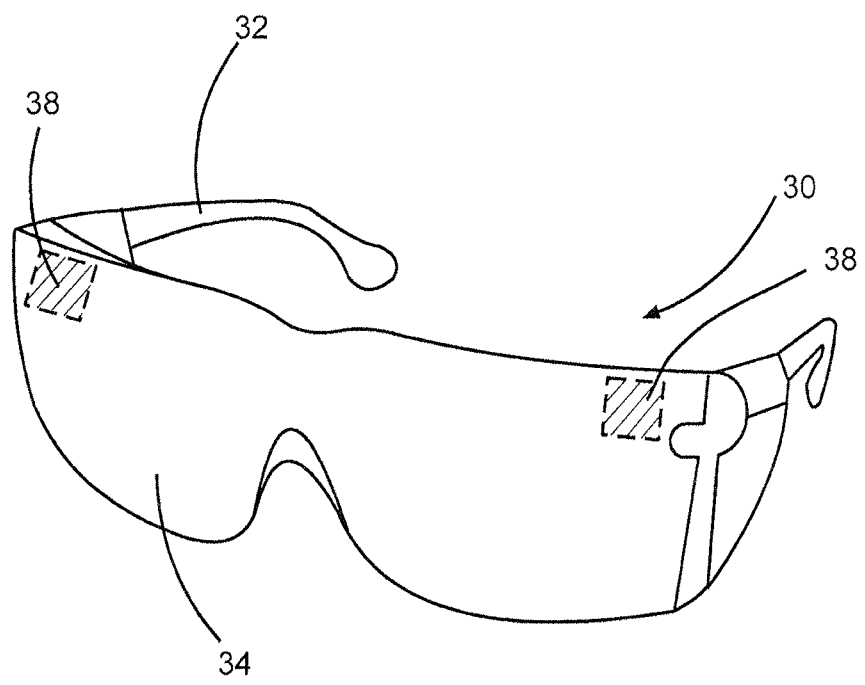

Referring generally to FIGS. 6A & 6B, safety glasses 30 are illustrated having frame 32 and lens 34. Safety glasses 30 such as those illustrated are commonly required in and around building, construction, and repair sites where welding operations occur. The safety glasses may also have one or more heat and/or UV exposure indicators 36. As shown in FIG. 6A, heat or UV exposure indicator 36 may be positioned on lens 34. Alternatively heat or UV exposure indicator may be positioned on frame 32. In one embodiment, the entire frame 32 may be a heat or UV exposure indicator. Upon exposure to thermal or UV radiation, exposure indicator 36 will change color or otherwise visually indicate the presence of thermal or UV radiation. As shown in FIG. 68, the indicator transitions to a darkened indicator 38. The thermal or UV exposure indicator may be formed from or include thermochromic or UV activated dyes as previously discussed. In one embodiment the indicator may be positioned on the outside of lens 34. In another embodiment the indicator may be positioned on the inside of lens 34. Positioning the indicator on the inside of the lens may provide a better indication of the amount of thermal or UV radiation reaching the eye. Both a person wearing the safety glasses 30 as well as other persons in and around the welding environment 10 may be alerted to the presence of excessive heat or UV radiation by the indicator 36.

Figure 7A:
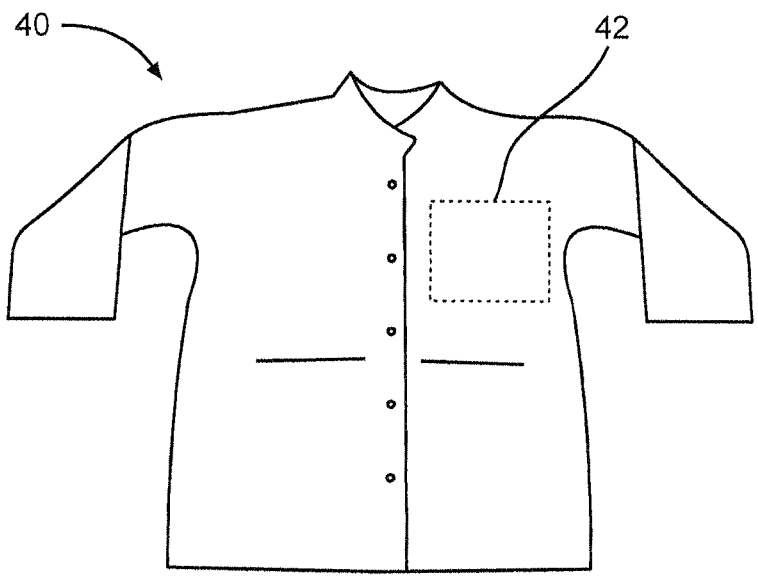
FIGS. 7A-B are perspective views of a welding jacket.
Figure 7B:
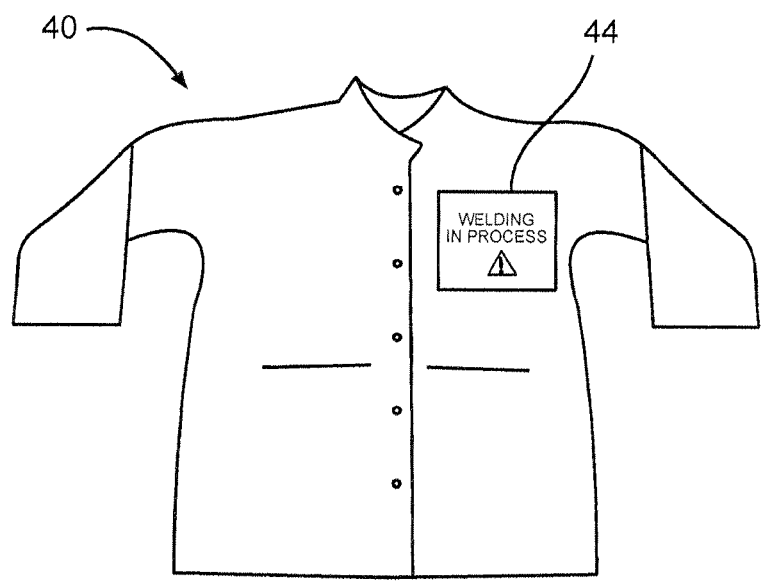

In yet another example, FIGS. 7A & 7B illustrate welding jacket 40 including a thermal or UV exposure indicator 42. Welding jacket 40 may be exposed to an electric welding arc and the thermal or UV radiation generated by the electric welding arc. Upon exposure, the indicator will transition from a first image to a second image upon exposure to an excessive amount of either heat or UV radiation. As shown in FIG. 7B, the second image may be a message 44 indicating that welding operations are in progress.

As previously explained, in a welding environment 10, welding system 14 may generate an electric welding arc between welding gun 16 or another welding apparatus and workpiece 18, where the electric welding arc generates excessive heat and/or UV radiation. Referring to FIGS. 2-4, a welding accessory, such as welding helmet 12, may have a thermal or UV exposure indicator. These indicators may be a portion of the outer surface 22 of welding helmet 22. Alternatively, UV exposure indicator may be a separate component, such as an adhesive backed indicator, that may be attached to the welding accessory.

The thermal or UV exposure indicator will have at least a first state and a second state. Referring to FIG. 2, a first state of the thermal or UV exposure indicator may be the undecorated outer surface 22 of welding helmet 12. A second state may be a symbol 26 or logo 28 appearing on the outer surface 22 of welding helmet 12 after exposure to either thermal or UV radiation (or both), as shown in FIGS. 3-4. Similarly, as shown in FIGS. 5A-5B, the first state may be a primary image 58 and the second state may be a secondary image 60 displayed along with the primary image 58.

The thermal or UV exposure indicator may provide a reversible visual indication upon exposure to heat or UV radiation. For example, the indicator portion of welding helmet 12 may transition from the primary image 58 to the secondary image 60 in the presence of heat and/or UV radiation, and may subsequently transition from secondary image 60 back to primary image 58 when the heat and/or UV radiation is no longer present. A thermal or UV activated dye may be selected to provide a desired degree of persistence for the second state. For example, the second state may be persistent for at least 2, 3, 5, 10, or 15 minutes or any other suitable time period after exposure to heat or UV radiation from the electric welding arc has ceased.

Figure 8A:
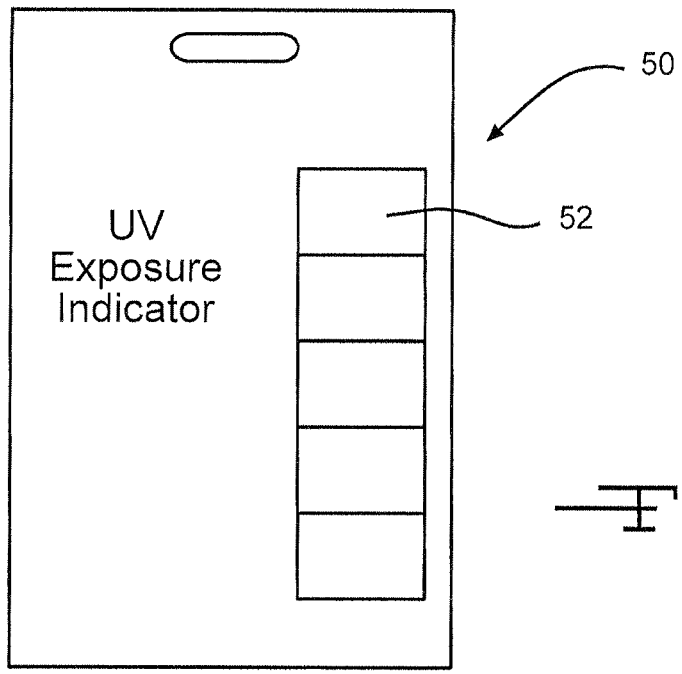
FIGS. 8A-B are perspective views of a UV indicator badge.
Figure 8B:
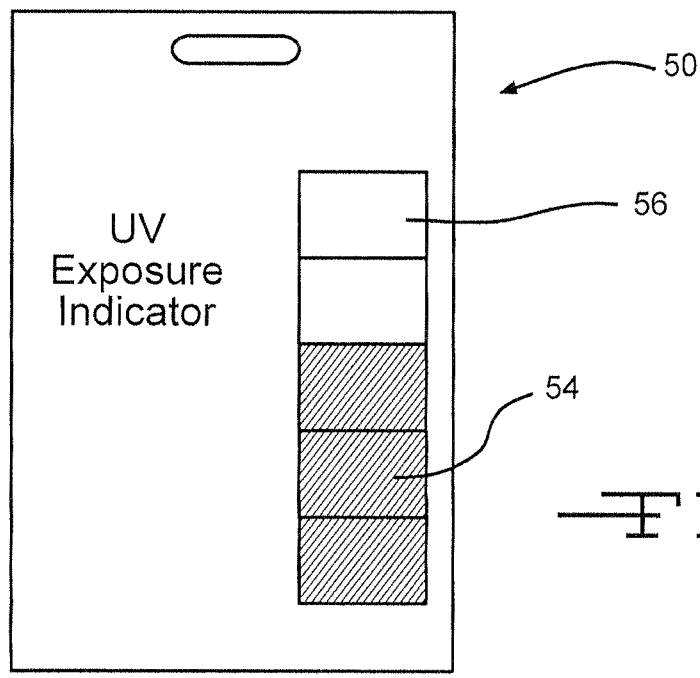

Referring to FIGS. 8A-8B as an example, a heat or UV exposure indicator may also have multiple states corresponding to the intensity of the associated heat and/or UV radiation exposure. In one example, the exposure indicator may be a badge 50 including graduated portion 52 serving as an exposure indicator and including one or more exposure-activated dyes. Graduated portion 52 may transition between a first state and a second state upon exposure to a predetermined intensity of radiation. Graduated portion 52 may transition to a third state and one or more additional states upon exposure to greater intensities of the appropriately-detected radiation (thermal or UV). For example, FIG. 8B illustrates badge 50 with an activated portion 54 and an unactivated portion 56 of graduated portion 52. As illustrated, graduated portion 52 may be divided into discrete sections each corresponding to a predetermined intensity of absorbed radiation, but discrete portions are not required and graduated portion 52 with a substantially continuous variation is contemplated.

The transition from the first state to the second state of the exposure indicator may comprise a visual indication, such as a change of color in the visual spectrum. The change of color may include changing between different colors or may include changing between different shades of a single color. As previously discussed, the second state may include a logo, symbol, text, or other decorative or informational design. The exposure indicator may be incorporated with a welding helmet, where the exposure indicator is integrated with the outer surface of the welding helmet. An exposure indicator as described herein may also be integrated with the inner surface of a welding helmet to indicate ingress of radiation inside the welding helmet during a welding operation. Such ingress of radiation may indicate a defect in the welding helmet reducing its effectiveness in protecting the eyes and head of the welder from radiation.

Other designs of exposure indicators are also possible. For example, an exposure indicator including an exposure-activated dye may be formed on a substrate with an adhesive backing, such as a sticker, and be applied to articles of clothing worn by personnel near a welding operation. Such indicators would provide a convenient means for monitoring exposure particularly for visitors or guests unaccustomed to working in a welding environment.

Also disclosed is a system for detecting cumulative radiation exposure during welding operations comprising a welding system adapted to generate an electric welding arc during a welding operation, the electric welding arc generating radiation; a welding accessory having an exposure indicator; and the exposure indicator having graduated states, the exposure indicator including an expsosure-activated dye adapted to provide a visual indication upon exposure to radiation generated by the electric welding arc, the visual indication being a transition between the graduated states to indicate cumulative exposure upon exposure to radiation generated by the electric welding arc during the welding operation.

As explained above, badge 50 may have a graduated portion 52 adapted to indicate levels of exposure by the transition between graduated states. Exposure-activated dyes are known that provide an irreversible change upon exposure to UV radiation. Such dyes may be referred to as photochangeable or photoreactive and are also commercially available. Exposure-activated dyes as used herein may also refer to these types of dyes.

The graduated portion 52 may be adapted to transition between states to indicate cumulative radiation exposure. Each section of graduated portion 52 may be selected to transition upon a predetermined level of radiation exposure. Persons working in or near a welding environment may therefore be able to monitor their cumulative radiation exposure and take appropriate preventative or protective measures to safeguard against the effects of such exposure.

Also disclosed is a method for detecting radiation exposure during a welding operation comprising providing a welding system adapted to generate an electric welding arc during a welding operation, the electric welding arc capable of generating UV and thermal radiation; providing an exposure indicator with at least a first state and a second state, the exposure indicator including an exposure-activated dye adapted to provide a visual indication upon exposure to radiation generated by the electric welding arc, the visual indication being a transition from the first state to at least the second state of the exposure indicator; operating the welding system to generate the electric welding arc generating radiation causing the exposure indicator to transition between at least the first state and the second state to indicate exposure to radiation from the electric welding arc; and monitoring the exposure indicator and ceasing the welding operation after a predetermined level of exposure is indicated on the exposure indicator.

As explained above, an exposure indicator may indicate both the presence of radiation and may be adapted to indicate the intensity of radiation. In some circumstances, it may be desired to cease welding operations when a predetermined level of radiation is present as indicated by the exposure indicator. Alternatively, additional protective measures, such as curtains or shields, may be required when radiation levels in the welding environment exceed predetermined levels. The method for detecting radiation exposure during a welding operation may thus provide information to the welding operator and the other persons in the welding environment to ensure that proper safety precautions are followed.

Also disclosed is a method for detecting cumulative radiation exposure during a welding operation comprising providing a welding system adapted to generate an electric welding arc during a welding operation, the electric welding arc capable of generating radiation; providing an exposure indicator with graduated states, the exposure indicator including an exposure-activated dye adapted to provide a visual indication upon exposure to radiation generated by the electric welding arc, the visual indication being a transition between the graduated states to indicate cumulative exposure; operating the welding system to generate the electric welding arc generating radiation causing the exposure indicator to transition between the graduated states to indicate exposure to a predetermined amount of radiation from the electric welding arc; and monitoring the exposure indicator and ceasing the welding operation after a predetermined level of cumulative exposure is indicated on the exposure indicator.

While certain embodiments have been described, it must be understood that various changes may be made and equivalents may be substituted without departing from the sprit or scope. In addition, many modifications may be made to adapt a particular situation or material to the teachings of the disclosure without departing from its spirit or scope.

What is claimed is:

1. A welding accessory comprising:
   a welding accessory surface for exposure to an electric welding arc during a welding operation, the surface having a first image and a second image,
   the first image being visible on the surface of the welding accessory without exposure to the electric welding arc, and
   the second image formed from a thermochromic-activated composition on the surface and visible only after exposure to thermal radiation generated by the electric welding arc during the welding operation and wherein the second image formed from a thermochromic-activated composition on the surface is reversible to be non-visible after withdrawal from exposure to the thermal radiation generated by the electric welding arc during the welding operation, and
   the second image formed from the thermochromic-activated composition on the surface is visible only after exposure to a predetermined amount of thermal radiation generated by the electric welding arc during the welding operation.

2. The welding accessory of claim 1, wherein
   the welding accessory is selected from the group consisting of welding helmets, welding jackets, hard hats, cloth skull caps, ball cap style hats, welding shirts, safety glasses, gloves, badges, work boots, belts, and jewelry.

3. The welding accessory of claim 1, wherein
   the thermochromic-activated composition is selected from the group consisting of a leuco material, a liquid crystal-based material, and an inorganic thermochromic composition.

4. The welding accessory of claim 1, wherein
   the thermochromic-activated composition is microencapsulated.

5. A system for detecting a threshold temperature of thermal radiation exposure during welding operations comprising:
   a welding system adapted to generate an electric welding arc during a welding operation, the electric welding arc generating thermal radiation;
   a welding accessory having a thermal exposure indicator; and
   the thermal exposure indicator having at least a first state and a second state, the thermal exposure indicator including a thermochromic-activated composition adapted to provide a visual indication upon exposure to a threshold temperature generated by the electric welding arc during the welding operation, the visual indication being a transition from the first state to at least the second state of the thermal exposure indicator upon exposure to thermal radiation generated by the electric welding arc during the welding operation; and wherein the welding apparel is a welding helmet, where the thermal exposure indicator is integrated onto the inner surface of the welding helmet to indicate ingress of thermal radiation inside the welding helmet during the welding operation, and further wherein the visual indication is reversible.

6. The system of claim 5, wherein the visual indication is a color change in the visual spectrum.

7. The system of claim 5, wherein the second state comprises a symbol.

8. The welding accessory of claim 5, wherein the welding accessory is selected from the group consisting of welding helmets, welding jackets, hard hats, cloth skull caps, ball cap style hats, welding shirts, safety glasses, gloves, work boots, belts, and jewelry.

9. The system of claim 5, wherein the welding accessory is a welding helmet, where the thermal exposure indicator is integrated with an outer surface of the welding helmet.

10. The system of claim 5, wherein the thermal exposure indicator is a sticker adapted to be applied to articles of clothing worn by personal near the welding operation.

11. The system of claim 5, wherein the thermal exposure indicator is selected from the group consisting of a leuco material, a liquid crystal-based material, and an inorganic thermochromic composition.

12. The system of claim 5, wherein the thermochromic-activated composition is microencapsulated.

13. The system of claim 5, wherein the thermochromic-activated composition provides a visual indication upon exposure to a predetermined amount of thermal radiation.

14. The system of claim 13, wherein the visual indication is persistent for at least about 2 minutes after exposure to thermal radiation.

15. The system of claim 5, wherein the thermal exposure indicator has graduated states, where the visual indication is a transition between the graduated states to indicate cumulative thermal exposure upon exposure to thermal radiation generated by the electric welding arc during the welding operation.

16. A method for detecting thermal radiation exposure during a welding operation comprising:

providing a welding system adapted to generate an electric welding arc during a welding operation, the electric welding arc capable of generating thermal radiation;

providing a thermochromic exposure indicator with at least a first state and a second state, the thermochromic exposure indicator including a thermochromic-activated dye adapted to provide a visual indication upon exposure to thermal radiation generated by the electric welding arc, the visual indication being a transition from the first state to at least the second state of the thermochromic exposure indicator;

operating the welding system to generate the electric welding arc generating thermal radiation causing the thermochromic exposure indicator to transition between at least the first state and the second state to indicate exposure to thermal radiation from the electric welding arc; and monitoring the thermochromic exposure indicator and ceasing the welding operation after a predetermined level of thermal exposure is indicated on the thermochromic exposure indicator.

17. A system for detecting thermal radiation exposure during welding operations comprising:

a welding system adapted to generate an electric welding arc during a welding operation, the electric welding arc generating thermal radiation;

a welding accessory having a means for indicating thermal exposure; and the means for indicating thermal exposure having at least a first state and a second state and including a means for providing a visual indication upon exposure to thermal radiation generated by the electric welding arc during the welding operation, the second state formed from the thermochromic-activated composition being visible only after exposure to a predetermined amount of thermal radiation generated by the electric welding arc during welding operations.

* * * * *